US009839603B2

(12) United States Patent
Andre et al.

(10) Patent No.: US 9,839,603 B2
(45) Date of Patent: Dec. 12, 2017

(54) DYESTUFFS OF PLANT ORIGIN AND USE THEREOF FOR COLOURING COMPOSITIONS, IN PARTICULAR COSMETIC COMPOSITIONS

(71) Applicant: LVMH RECHERCHE, Saint Jean de Braye (FR)

(72) Inventors: Patrice Andre, Neuville aux Bois (FR); Michel Garcia, Lauris (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 206 days.

(21) Appl. No.: 14/146,985

(22) Filed: Jan. 3, 2014

(65) Prior Publication Data
US 2014/0120045 A1    May 1, 2014

Related U.S. Application Data

(63) Continuation of application No. 12/990,435, filed as application No. PCT/FR2009/050794 on Apr. 29, 2009, now abandoned.

(30) Foreign Application Priority Data

Apr. 29, 2008  (FR) ..................... 08 52905

(51) Int. Cl.
| | | |
|---|---|---|
| *A61K 8/97* | (2017.01) | |
| *A61Q 1/10* | (2006.01) | |
| *A61Q 19/08* | (2006.01) | |
| *C09B 61/00* | (2006.01) | |
| *A61Q 1/02* | (2006.01) | |
| *A61Q 3/00* | (2006.01) | |
| *A61Q 5/00* | (2006.01) | |
| *A61Q 19/00* | (2006.01) | |
| *A61Q 5/06* | (2006.01) | |
| *C09B 67/54* | (2006.01) | |

(52) U.S. Cl.
CPC ............. *A61K 8/97* (2013.01); *A61Q 1/02* (2013.01); *A61Q 1/10* (2013.01); *A61Q 3/00* (2013.01); *A61Q 5/00* (2013.01); *A61Q 5/065* (2013.01); *A61Q 19/00* (2013.01); *A61Q 19/007* (2013.01); *A61Q 19/08* (2013.01); *C09B 61/00* (2013.01); *C09B 67/0096* (2013.01)

(58) Field of Classification Search
CPC ... A61K 8/97; A61Q 1/10; A61Q 1/02; A61Q 3/00; A61Q 5/65; A61Q 5/00; A61Q 18/00; A61Q 18/08; A61Q 18/007; C09B 61/00; C09B 67/0096
See application file for complete search history.

(56) References Cited

U.S. PATENT DOCUMENTS

| | | | |
|---|---|---|---|
| 3,333,962 A | * | 8/1967 | Prebluda .............. A23K 1/1606 424/764 |
| 7,023,552 B2 | | 4/2006 | Simon et al. |
| 2003/0115687 A1 | * | 6/2003 | Belcour-Castro .... C07D 239/46 8/406 |

FOREIGN PATENT DOCUMENTS

| | | |
|---|---|---|
| CN | 101 121 631 | 2/2008 |
| EP | 1 191 071 A1 | 3/2002 |
| JP | 2003-277641 | 10/2003 |
| JP | 2007-112931 | 5/2007 |
| WO | WO 2008/129215 | 10/2008 |

OTHER PUBLICATIONS

Agarwal et al. Derwent 1997-089275, 1997.*
Inventory of seeds and plants imported, issue 46, 1916, p. 85.*
Pirone "Aril Structure and Pigments in the Strelitziaceae" Jul. 31, 2006.*
Lee et al., "Structural fruit coloration in Delarbrea Michieana (Araliaceae)," *Int. J. Plant Sci.* (2000) 161 (2): 297-300.
Lee et al., "Physical basis and ecological significance of iridescence in blue plants," *Nature* (1975) 254: 50-51.
Prione, C., "Aril structure and pigments in the strelitziaceae (Abstract ID: 564)," *Botany* (2006): California State University. XP002516321. Abstract Only.
Prione, C., "Two unique aril pigments in the strelitziaceae (order: Zingberales) (Abstract ID: 2108)," *Botany & Plant Biology* (2007). XP002516320. Abstract Only.
Invewntory of seeds and plants imported, issue 46, 1916, p. 85.
ZFIN phenotype statement Jan. 26, 2013.

* cited by examiner

*Primary Examiner* — Amina Khan
(74) *Attorney, Agent, or Firm* — Merchant & Gould P.C.

(57) ABSTRACT

The invention relates to a dyestuff of plant origin, obtained from a colored part of a plant species, the cell tissues of which contain iridisomes responsible for the coloration of said part. It relates most particularly to a blue dyestuff obtained from the arils of the seeds of the plant species *Ravenala madagascariensis*. It also relates to compositions, in particular cosmetic compositions, especially intended for making up the skin or superficial body growths, containing said dyestuff.

7 Claims, No Drawings

DYESTUFFS OF PLANT ORIGIN AND USE THEREOF FOR COLOURING COMPOSITIONS, IN PARTICULAR COSMETIC COMPOSITIONS

This application is a Continuation Application of U.S. Ser. No. 12/990,435 filed 10 May 2011, now abandoned, which is a National Stage Application of PCT/FR2009/050794, filed 29 Apr. 2009, which claims benefit of Serial No. 0852905, filed 29 Apr. 2008 in France and which applications are incorporated herein by reference. To the extent appropriate, a claim of priority is made to each of the above disclosed applications.

The subject of the present invention is novel dyestuffs of plant origin, and also the use thereof for coloring compositions, in particular cosmetic compositions.

The invention applies most particularly to the preparation of colored cosmetic compositions, in particular intended for making up the skin or superficial body growths. It also applies to colored compositions of any type for other industrial fields, such as the field of food products, that of medicaments, inks, dyes, paints and products applicable in the graphic arts field and the decorating field in general.

PRIOR ART

The term "pigments" generally denotes coloring substances which are insoluble in the medium that they color.

In general, in the cosmetic field, two types of pigments are used.

More specifically, pigments, in particular of plant, animal or mineral origin, which cause a coloration effect by selective absorption of certain wavelengths of the incident light when they are dispersed in a medium, for example a cosmetic composition, are used in the cosmetics field, and most particularly for makeup.

Among the pigments of plant origin, mention will be made of indigo, an extractable coloration substance obtained by fermentation of *Indigofera suffruticosa* or *Indigofera tinctoria* leaves.

It should be noted that indigo is virtually insoluble in water and in alcohol.

Mention will also be made of compounds of anthocyan type, optionally modified with metal cations.

The coloration effect induced by these pigments dispersed in a medium is caused by a phenomenon of selective absorption of certain wavelengths of the incident light by these compounds.

The light supplementary to the absorbed light is scattered by the material and determines the color thereof.

The color thus produced is often called "pigment color".

These pigments are widely used for preparations in many industrial fields, for example in the field of inks or paints, but also in the cosmetics industry, in particular for makeup.

The article by Cary Pirone entitled "Aril Structure and pigments in the Strelitziaceae (abstract id: 564) published in Botany 2006, of Jul. 28, 2006, available in the form of an extract on the internet http://www.2006.botanyconference.org/engine/search/index.php, relates to pigments extracted from the plant *Ravenala madagascariensis*, the chemical structures of which have not yet been identified.

However, the pigment has been identified as being a pigmentary complex of proteins which is blue in color.

A second article by the same author Cary Pirone is published in Botany Interbiology 2007, of Jul. 7, 2007, extract available on the internet http://www.2007.botanyconference.org/engine/search/index.php.

In this case, it is indicated that the research relates more specifically to the identification of two unusual pigments, one orange and the other yellow, found in *P. Guayanense* and *S. Nicolai*, the chemical structure of which has been identified by mass spectrometry and by NMR.

The abstract in Database WPI Week 200741, reference AN 2007-427 923 refers to Japanese application JP 2007 112 931 from Toyo Ink Manufacturing Co Ltd which relates to a blue pigment obtained by extraction with an alcoholic organic solvent, an aliphatic ketone, etc, added to an extract of *Clitoria ternatea* flowers, which it is possible to use as an additive for food, cosmetic products, pharmaceutical products and inks.

Furthermore, the article by Lianfu Zhang entitled "Method for fast extracting lycopene", referenced in Database WPI Week 2008, AN 2008-M13793, refers to a patent application CN 101 121 631 from the Jiangnan University published on Feb. 13, 2008 for the extraction of lycopene.

Furthermore, the abstract published in Database WPI reference AN 2003-857 780 refers to an application JP 2003/277 641 from Ichimaru Pharcos Inc relating to a new pigment derivative extracted from lithospermum roots, which does not have a skin contact allergy property, which has a notably improved pH stability range, good heat stability and filterability, and which is used as a dye for cosmetic compositions. It is specified that the lithospermum root pigment derivative is a complex formed by adding a solution containing an ion of a metal chosen from aluminum, iron, magnesium, zinc, copper and manganese, a dicarboxylic acid compound and a plant protein hydrolysate (see abstract of this document).

Furthermore, document EP 1 191 071 relates to an anthocyantin coloring agent and a method for the production thereof from organic matter.

Finally, document WO 2008/129215 (Diana Naturals) relates to a coloring food composition containing modified colorings of the anthocyanin family and to a process for bathochromic modification of these colorings.

In the cosmetics field, a second type of pigment of natural or synthetic origin, consisting of nacres, is also available. This second type of pigment acts via a different mechanism to confer the coloration on the composition, since the production of colors is linked in this case to a phenomenon of undulatory interference of the light reflected on the surface of the nacre.

This other color production mode is not linked to a mechanism of absorption of light by a chemical substance, but to a phenomenon of undulatory interference of the light reflected on structures present at the surface of the object observed.

These superficial structures thus produce a coloration effect, called iridescence, characterized by colors which change according to the angle of observation or according to the angle of incidence of the illuminating light.

These colors differ from pigment colors and are often denoted under the term "structural colors".

This second color production mode is present in many animal species, in particular among insects and birds.

By way of example, mention will be made of certain colors of bird feathers or of butterfly wings.

However, although structural colors are quite frequently present in the animal kingdom, they are very rare in the plant world and have been detected only very recently and in a limited number of plant species.

The discovery of colors produced by interference, in some rare plant species, has thus led researchers to take a new look at the colors derived from the plant world and to wonder about the ecological advantage for the plant in developing such iridescent colorings (Lee et al, Nature, 1975, 2445, 50-51).

Even though, at the current time, the iridescence phenomenon and the structures which are responsible for it are not completely elucidated, it has been possible to establish that ultrastructures generally called "iridisomes" are responsible for the colored effect of the product resulting from a phenomenon of light interference at its surface.

Among the plant species of which some cell tissues comprise iridisomes, mention may be made of the plant species of the family Strelitziaceae, in particular the plant species *Ravenala madagascariensis*, plant species of the family Elaeocarpaceae, for example *Elaeocarpus angustifolius* Blume, plant species of the family Arraliaceae, in particular the plant species *Delarbrea michieana*, plant species of the family Marattiaceae, in particular the plant species *Danaea nodosa*, plant species of the family Hymenophyllaceae, in particular the plant species *Trichomanes elegans*, plant species among those of the *Selaginella* genus, for example *Selaginella willdenowii*, plant species of the family Athyriaceae, in particular the plant species *Diplazium tomentosum*, plant species of the family Lindsaeaceae, in particular the plant species *Lindsaea lucida*, plant species of the family Begoniaceae, in particular the plant species *Begonia pavonina*, plant species of the family Melastolataceae, in particular the plant species *Phyllagathis rotundifolia*.

Researchers have identified and studied such ultrastructures in the epidermal cells of the fruit of the Australian plant species *Delarbrea micheana* (Lee D W et al., Int. J. Plant Sci, 2000, 161 (2), 297-300).

The authors have put forward the hypothesis of a coloration produced by a "constructive" interference phenomenon.

This interference phenomenon is caused by a region of the superficial cells of the epidermis of the plant, which are in the form of a cellulose-based, complex, multilayer structure.

The visual effect produced by the plant is thus dependent on the thickness of these multilayers responsible for the light interference mechanism, said thickness being estimated at a few tens of nanometers.

In the case of the species *Delarbrea micheana*, these ultrastructures are located in the cells of the epidermis of the plant, in the region close to the outside environment, and have a thickness estimated at approximately 75 nm.

Although they are still incompletely characterized, it appears that these plant ultrastructures responsible for the colored effect produced by the plant are constituted of thin layers of hydrated cellulose and/or of helicoidal arrangements of cellulose fibrils, producing in this case a homogeneous colored effect irrespective of the angle of observation, owing to their spatial distribution.

The colors and shades thus obtained are original, such that the use of such plant ultrastructures as structural pigments could represent an alternative to the conventional coloring processes using colorings or pigments in the form of extractable and purified molecules or aggregates.

However, up until now, the use of these plant ultrastructures as colored pigments has never been envisioned owing to the fact that the colored effect comes from a fragile arrangement of macromolecules capable of being degraded during the implementation of the extraction process.

PURPOSES OF THE INVENTION

A main purpose of the present invention is to provide a dyestuff from a colored plant material comprising plant ultrastructures without denaturing them.

A second main purpose of the invention is to provide a dyestuff from a colored plant material comprising plant ultrastructures without denaturing them, in such a way as to integrate them into compositions, in particular into cosmetic compositions, with a view to conferring, on the latter, a color which is essentially the color of the colored part of the treated plant.

A third main purpose of the invention is to provide a method for reliable, reproducible and also inexpensive production of this dyestuff from a colored plant material comprising plant ultrastructures without denaturing them.

The invention makes it possible to solve, for the first time, these technical problems in an unexpected, safe and reliable manner which can be used on the industrial and cosmetic scale.

SUMMARY OF THE INVENTION

Entirely surprisingly, the inventors of the present invention have succeeded in extracting, from plant tissues comprising these plant ultrastructures, a colored product, hereinafter denoted "dyestuff of the invention", the very vivid color of which is that of the colored part of the treated plant.

The term "dyestuff of the invention" denotes the colored product obtained after extraction of the plant tissue from which it is desired to extract the color. This colored product has the characteristic color of the treated plant tissue, said color being linked to the presence of the plant ultrastructures or "iridisomes", as disclosed above.

In addition to the possibilities of identifying these ultrastructures by techniques such as electron microscopy or X-ray fluorescence spectrometry, those skilled in the art will be able to ascertain that these ultrastructures responsible for the coloration are not degraded by visual monitoring.

Thus, the dyestuff of the invention comprises the plant ultrastructures directly responsible for the colored effect which constitute the essential part of this dyestuff. However, it can also comprise a fraction termed "auxiliary fraction", or alternatively "auxiliary part", extracted from the plant at the same time as the iridisomes, it being possible for this fraction to be of a varied nature depending on the plant from which the dyestuff of the invention is extracted. This auxiliary fraction, which does not contribute directly to the colored effect, can play the role of a carrier, a support or a stabilizer and does not need to be eliminated during the preparation of a colored composition. It may in fact be found that the presence of this auxiliary fraction facilitates the handling of the dyestuff of the invention or confers thereon a supplementary effect which is useful, for example, for improving the texture of the composition to which the dyestuff is added in order to color it.

Without wishing to anticipate the results of the structural characterization of the dyestuffs extracted, it clearly appears, at this time, that the coloration of the product of the invention is linked to the non-denaturation of the plant ultrastructures present in the iridisomes which are consequently contained in the dyestuff of the invention.

Thus, the inventors of the present invention have been able to extract a dyestuff from a colored plant material comprising plant ultrastructures without denaturing them, and to integrate them into compositions, with a view to conferring on the latter a color which is that of the colored part of the treated plant.

Thus, the extraction of the dyestuff of the invention from a colored plant material comprising iridisomes makes it possible to implement an innovative technique for coloring compositions of a varied type, such as cosmetic compositions, medicaments, food products, inks, dyes, paints and products applicable in the graphic arts field and the decorating field in general.

The dyestuffs thus obtained are capable of giving the compositions into which they are introduced new shades.

These dyestuffs furthermore exhibit a stability and an innocuousness which offer an additional guarantee that the intrinsic qualities of the compositions, in particular cosmetic compositions, in which they are dispersed will be preserved.

Finally, they are insoluble in water and in all the solvents normally used, and are compatible with the nonaqueous adjuvants normally used in cosmetic compositions, thereby making their use particularly advantageous as colored pigments dispersed in a cosmetic composition.

The invention thus relates to a colored plant extract, said extract being obtained from a plant material formed by or comprising colored cell tissues, themselves comprising iridisomes.

More specifically, the invention relates to a new dyestuff which owes its colored and coloration qualities to the fact that the inventors of the present invention have been able to develop a method for extracting the structure responsible for the coloration of the plant material, without degrading it, thus resulting in a stable, colored product which can be used as a pigment, in particular in the cosmetics field.

The invention also relates to the method used for extracting this dyestuff of plant origin without denaturing it.

The invention also relates to cosmetic compositions, in particular intended for makeup, containing such dyestuffs.

The invention also relates to a method for coloring a composition, in particular a cosmetic composition, especially intended for makeup.

The invention also relates to a makeup process comprising the application of a cosmetic composition containing such a dyestuff.

DETAILED DESCRIPTION OF THE INVENTION

More specifically, according to a first subject, the invention relates to a dyestuff of plant origin obtained from a colored part of a plant species, the cell tissues of which contain iridisomes responsible for the coloration of said part. This dyestuff can be in a waxy, solid or pasty form. In the case of obtaining a blue dyestuff, the latter is advantageously obtained from the arils of the plant species *Ravenala madagascariensis*.

According to a second subject, the invention relates to colored compositions, especially cosmetic compositions, in particular coloring cosmetic compositions intended for making up the skin or superficial body growths, containing a dispersion of the dyestuff of plant origin of the first subject.

According to a third subject, the invention relates to a method for extracting the dyestuff of plant origin of the first subject.

According to a fourth subject, the invention relates to a method for preparing a colored or coloring composition, in particular a cosmetic composition, comprising the introduction, into said composition, of at least one dyestuff of the first subject of the invention or obtained by means of the method of the third subject of the invention.

According to a fifth subject, the invention relates to a process for making up the skin or superficial body growths, such as the eyelashes, the hair or the nails, comprising the application, to at least a part of the skin or superficial body growths, of the cosmetic composition of the second subject or prepared according to the fourth subject or containing the dyestuff of the third subject.

According to a particularly advantageous variant of all these aspects, the plant material from which the dyestuff of the invention is prepared is constituted of the arils of the seeds of the plant species *Ravenala madagascariensis*.

It is understood that the second and fourth subjects of the invention defined above that are applicable to colored or coloring cosmetic compositions can, without difficulty for those skilled in the art, be applied to compositions of many other fields, such as medicaments, food products, inks, dyes, paints and products applicable in the graphic arts field and the decorating field in general.

Other characteristics and advantages of the invention will become apparent on reading the detailed description hereinafter and the examples which follow.

As has been previously disclosed, the invention results from the discovery by its inventors that it was possible to prepare a dyestuff from a colored part of a plant species, the cell tissues of which contain iridisomes responsible for the coloration of this part of the plant species.

As disclosed previously, the iridisomes responsible for the coloration of the plant from which the dyestuff of the invention is extracted are known to be constituted of particularly fragile ultrastructures. The obtaining of the dyestuff of the invention therefore requires the implementation of a particularly mild method in which the structure of the iridisome is respected.

It became apparent to the inventors of the present invention that, to this effect, it was particularly advantageous to subject the part of the plant species containing the iridisomes responsible for the coloration to a step during which the plant cells included in the cell tissues containing the iridisomes are at least partially decompartmentalized in the presence of a liquid medium, so as to release a colored product and to entrain it by means of this liquid medium.

The production of a colored effect by these iridisomes appears to require that said iridisomes have a structure after extraction which is unaltered compared with the structure of the same iridisomes in the cell tissues of the plants or parts of plants in which they produce the colored effect.

The iridisomes present in the liquid medium in which they are collected, provided they have retained their nondenatured and functional state, produce a coloration in the region or identical to that of the cell tissue from which these structures are extracted.

In order to at least partially decompartmentalize the plant cells, at least one external energy source is advantageously used.

According to one particularly advantageous variant of the invention, the at least partial decompartmentalization of the plant cells is carried out by means of at least one external energy source, in particular by mechanical stirring, for example using a magnetic stirrer, a homogenizer or a mill.

According to another particularly advantageous variant of the invention, the at least partial decompartmentalization of the plant cells is carried out under the effect of ultrasound, in the presence of a liquid medium.

The use of ultrasound has proved to be particularly effective in the context of the present invention.

Specifically, under the effect of ultrasound in a liquid, microbubbles form through the well-known cavitation effect.

These microbubbles are pulsed by the ultrasound waves and as a result grow to a critical size, after which they implode and then restore, during this collapse, their energy in the form of a shockwave.

Those skilled in the art will have no difficulty in adjusting the frequency of the ultrasound, in routine tests, in particular by controlling the color of the entrained liquid. Of course, the optimum frequency will depend on the plant material treated.

Thus, in the case of the preferred plant material used according to the invention, namely the arils of the seeds of *Ravenala madagascariensis*, frequencies in the region of 27 kHz will preferably be chosen.

In order to more effectively decompartmentalize the plant cells, it is also possible to subject the plant material to mechanical stirring combined with the application of ultrasound.

The purpose of the application of the ultrasound or of any other means of at least partial decompartmentalization of the plant cells is to release the ultrastructures responsible for the coloration without denaturing them, so as to release a colored product.

The liquid medium thus entrains the released structure, separating it from the cellulose which can be subsequently eliminated, for example by filtration.

Thus, the liquid medium is then advantageously subjected to a filtration step intended to free the product of the invention of at least a part of the cellulose-based residues which will remain on the filter.

In general, the dyestuff according to the invention is prepared according to a method which makes it possible to isolate the iridisomes from the plant material without denaturing the structure thereof which is responsible for the effect of coloration by constructive interference.

According to an optional variant of this method, the plant material is treated, prior to the extraction step itself, so as to remove a part of the waxy material contained in said plant material, by means of a suitable method. This pretreatment of the plant material can advantageously be carried out using $CO_2$ in the supercritical or subcritical state. The partially "dewaxed" plant material is then subjected to the extraction step as described above in order to collect the iridisomes and the remaining wax fraction. The optional pretreatment step makes it possible to obtain a dyestuff of which the visual properties differ substantially from the product obtained without pretreatment, by modifying the respective proportions of iridisomes and of waxy material in the dyestuff finally obtained.

The invention thus also relates to a method for extracting the iridisomes responsible for the colored effect, which method does not denature the structure thereof.

As emerges from the disclosure which follows, the iridisomes may be extracted in combination with an auxiliary fraction of the plant material.

The presence of iridisomes in colored tissues of plants can be demonstrated by various means known to those skilled in the art, in particular by electron microscopy or X-ray fluorescence spectrometry.

In one preferred embodiment of the invention, the colored cell tissue of plant origin comprising said structures is subjected to ultrasound in a liquid medium, the result of this step being a decompartmentalization of the plant cells under the effect of the microbubbles formed by cavitation.

Under the effect of the microbubbles thus formed, the structures responsible for the coloration detach from the plant cells in which they are stored, without being denatured.

As previously disclosed, a certain number of plant species of which a part of the tissues contain iridisomes are known in the literature.

All these parts of plants can be treated using the method of the invention in order to prepare the dyestuff of the invention.

Thus, the plant species is advantageously chosen from the group constituted of plant species of the family Strelitziaceae, in particular the plant species *Ravenala madagascariensis*, plant species of the family Elaeocarpaceae, for example *Elaeocarpus angustifolius* Blume, plant species of the family Arraliaceae, in particular the plant species *Delarbrea michieana*, plant species of the family Marattiaceae, in particular the plant species *Danaea nodosa*, plant species of the family Hymenophyllaceae, in particular the plant species *Trichomanes elegans*, plant species among those of the *Selaginella* genus, for example *Selaginella willdenowii*, plant species of the family Athyriaceae, in particular the plant species *Diplazium tomentosum*, plant species of the family Lindsaeaceae, in particular the plant species *Lindsaea lucida*, plant species of the family Begoniaceae, in particular the plant species *Begonia pavonina*, plant species of the family Melastolataceae, in particular the plant species *Phyllagathis rotundifolia*.

The plant part chosen for preparing the dyestuff of the invention depends, of course, on the plant species selected.

Thus, the plant material can be a plant part or the whole plant, but can in particular be constituted of a part of a fruit, a part of a seed or a part of a leaf, or of a whole fruit, of a whole seed of or a whole leaf, on the condition that the plant material comprises or is formed from a colored cell tissue comprising iridisomes.

The cell tissue is preferably formed by the superficial cell layers of the part of the plant which has a colored effect by interference, and in particular by the cell layers at the external surface of the plant part, for example the cells of the epidermis of the plant.

The tissue can be formed, for example, and in a nonlimiting manner, by the epidermis of the fruit, by the seed coat, or by the surface tissue of a leaf.

For the Malaysian rainforest plants studied by Lee in the publications mentioned above, the tissue is formed of leaves.

The liquid medium in which the extraction is carried out is formed of a solvent or a mixture of solvents in which the iridisomes are insoluble but which will make it possible to entrain them alone or in combination with a fraction of the plant material, itself separated from the constitutive cellulose of the plant tissue under the effect of the ultrasound.

Those skilled in the art will readily understand that the composition of the liquid medium in which the decompartmentalization of the cells of the plant tissue is carried out is chosen according to the nature of the plant tissue, this choice being made in order to entrain a colored product, optionally associated with a part of the plant material.

Those skilled in the art will also readily understand that any part of the plant material which does not contribute to the colored effect and which has been entrained during the extraction should not harm the colored effect obtained or should be able to be subsequently eliminated during at least one step of purification of the dyestuff of the invention, before the use thereof.

The part finally retained constitutes what is denoted, without distinction, "auxiliary part" or "auxiliary fraction" in the sense of the invention, as previously disclosed. The liquid media are preferably those in which cellulose is insoluble and nondenatured, and are in particular chosen from aqueous solutions of alkalis, acetone, ethyl acetate, plant essential oils, liquid alkanes normally used as extraction solvents, in particular cyclohexane and heptane.

These liquid media can in particular be chosen from those which those skilled in the art use to carry out a method for extracting thin layers, insofar as said liquid media do not attack the cellulose support.

The method for obtaining the dyestuff of the invention also advantageously comprises a step during which the liquid medium recovered at the end of the decompartmentalization step is filtered so as to eliminate the plant residues and make it possible to collect the structures responsible for the colored effect (iridisomes) optionally in the presence of an auxiliary fraction as previously defined.

After elimination of the plant residues, the coloring plant structures (essentially constituted of iridisomes) are collected and purified according to procedures conventionally used, so as to form a plant extract capable of being used as a pigment in compositions of any type that may include the same.

According to a first alternative, this step is carried out by direct elimination of the solvent or of the mixture of solvents forming the liquid extraction medium.

According to a second possible implementation, the liquid medium constituted of the organic phase is cooled and cold water is added thereto. The coloring structures are released from the organic phase and flocculate in the aqueous phase. These coloring structures are then readily collected by filtration.

A step of purifying the dyestuff is then optionally carried out, for example by eliminating the solvent(s) forming the liquid medium in which said dyestuff was extracted.

Only the broad outlines of the extraction method as defined above can of course be given, considering the variety of the plant materials concerned.

Those skilled in the art will readily understand that this method will have to be adapted according to the plant material treated so as to provide a dyestuff that can be used as a pigment in colored compositions, in particular in cosmetic compositions.

As previously disclosed, it may be advantageous to entrain, by means of the liquid medium used for carrying out the method of the invention, not only the structure responsible for the coloration, but also one or more other substances of the plant material, termed auxiliary fraction.

This is in particular the case when the iridisomes are included in a wax fraction of the colored part of the plant species.

In such a case, the method can be adapted by choosing, as liquid medium, a suitable solvent or mixture of solvents so as to simultaneously extract the structure responsible for the coloration, i.e. a dyestuff which can be in a waxy, solid or pasty form, and the waxy product, with the possibility of using this mixture or this dyestuff directly in a cosmetic composition subsequently formed.

Thus, as emerges from the detailed description which follows, in the particular case of the dyestuff extracted from the arils of the seeds of the plant species *Ravenala madagascariensis*, which constitutes the preferred dyestuff according to the invention, advantage is taken of the fact that the iridisomes are contained in a waxy part of the plant.

*Ravenala madagascariensis* (also called traveler's palm, *Ravenala Urania speciosa* or *Urania madagascariensis*) is a herbaceous plant with a lacunal stem, the trunk of which, at maturity, is approximately ten meters high, which brings its total height to approximately 20 meters.

The fruits are very hard capsules with 6 cavities containing numerous seeds, each surrounded by a coat, also called aril, the vivid blue color of which is quite rare among plants.

These arils contain close to 50% by weight of a waxy fraction about which little is still known.

In this particular case, the method is advantageously adapted so as to extract, at the same time, the structure responsible for the blue coloration (iridisome) and the wax.

The description which will follow is given in the case of the preferred example (arils of the seeds of the plant species *Ravenala madagascariensis*). The method described can nevertheless be directly adapted to various plants in which the part containing the iridisomes also contains a wax.

According to a preferred variant of the invention, the dyestuff extracted from the arils of the seeds of the plant species *Ravenala madagascariensis* is a blue pigment.

Specifically, this preferred variant of the present invention is based on the demonstration of the presence of iridisomes in colored plant tissues derived from a plant of the species *Ravenala madagascariensis*, which is a tropical plant species belonging to the family Strelitziaceae.

The invention thus relates, according to a preferred variant, to a colored plant dyestuff obtained from a plant material formed by, or comprising, arils of seeds of the plant species *Ravenala madagascariensis*.

This preferred dyestuff of the invention is prepared according to a method which makes it possible to extract the iridisomes from the cell tissues of the seed coat without denaturing said iridisomes.

The extract thus obtained is blue in color.

According to this preferred variant of the method for preparing this dyestuff, the plant material formed by or comprising the arils of the plant species *Ravenala madagascariensis* is subjected to mechanical stirring and/or to the action of microbubbles formed by the application of ultrasound in a liquid medium.

For all these plant materials which have a waxy nature, the decompartmentalization method is carried out, in particular, under the effect of ultrasound, in the presence of a liquid medium chosen so as to entrain the waxy material and the colored structures (iridisomes), in the form of a colored product.

According to a first advantageous variant of this method, the liquid medium chosen is a solvent for the waxy material.

A particularly preferred medium is acetone.

According to one advantageous variant, this method comprises a step of precipitation of the colored product, in particular by cooling of the liquid medium.

According to this variant, water is added to the liquid organic medium, in particular acetone, in order to cause the wax to be released, and the mixture is cooled. The wax then flocculates and entrains the colored pigment.

The colored wax extract is then filtered, washed and dried.

Another particularly advantageous variant of the method is also applicable to plant materials containing a waxy material.

This variant proves to be particularly advantageous in that it makes it possible to avoid the use of solvent, the complete elimination of which is sometimes tricky.

According to this variant, the liquid medium is an alkaline medium which makes it possible to saponify the waxy material, so as to recover a colored basic solution containing the waxy material in saponified form and also the colored structures.

In this case, aqueous ammonia solution is preferably used to carry out the saponification step.

The liquid medium constituted of the colored basic solution containing the dyestuff of the invention is then subjected to a step of washing with an acidic solution, so as to cause the waxy material to flocculate.

This second type of method essentially aims to extract a colored wax containing the dyestuff of the invention.

When the wax is saponified under the action of the basic solution, it makes it possible to facilitate the extraction of the ultrastructures.

Thus, the colored wax is obtained in two stages according to this method:
- a first stage during which the basic solution extracts a wax/colored compound "complex" which is filtered, and
- a second stage during which the basic medium of the preceding step is acidified with an organic acid, for example acetic acid, so as to precipitate a "complex" product comprising waxy material, insoluble in an acidic medium, which entrains, at the time of its precipitation, the thin layers responsible for the colored phenomenon; this complex is subsequently washed, then filtered and dried.

In the case of the plant species *Ravenala madagascariensis*, the wax-rich arils are preferably treated according to a method which makes it possible to extract the iridisomes at the same time as the wax: preferably, the arils are treated with ultrasound in aqueous ammonia solution. Preferably, 1 ml of aqueous ammonia at 20% (22° Be) per liter of water will be used and the temperature is kept at approximately 60° C. for 10 min. This extraction can be repeated once. The wax is saponified and entrained with the iridisomes. The liquids are filtered and neutralized with acetic acid.

During the abovementioned acidification step, the volume of acetic acid is advantageously adapted so as to adjust the pH to a value in the region of 4, or even less than 4, which makes it possible to adjust the size of the wax flakes which precipitate and facilitates the recovery thereof.

The waxy blue mass which precipitated is filtered off; it is rinsed on a filter and dried at a moderate temperature.

According to an optional variant of this method, the *Ravenala madagascariensis* arils are treated using $CO_2$ in the supercritical or subcritical state, prior to the extraction itself.

Another subject of the invention relates to the use of the dyestuff of the invention, as a pigment in colored compositions capable of including the same.

Thus, the invention relates to colored compositions, in particular cosmetic compositions, containing a dispersion of dyestuff as defined above, acting as a pigment.

The compositions are defined as compositions in which the coloring agent retains its coloring properties without the other compounds denaturing the particular structure thereof.

In the cosmetic field, this composition may be in the form, for example, of a serum, a lotion, an emulsion, such as a care cream, a hydrogel, such as a mask, or a mascara, a foundation, an eye shadow or an eyeliner, a stick, or else a patch.

The preferred compositions are those comprising fatty adjuvants, or even nonaqueous or essentially water-free adjuvants.

The cosmetic compositions containing the dyestuff of the invention advantageously comprise at least one cosmetically acceptable active agent and at least one cosmetically acceptable excipient.

The colored cosmetic composition may be a skincare product, and the coloring cosmetic composition will be a product for making up the skin or superficial body growths.

The colored cosmetic compositions which comprise the coloring agent according to the invention may comprise at least one cosmetically active agent chosen from substances which have a depigmenting activity or a lightening activity on the skin; substances which have a slimming activity; substances which have a hydrating activity; substances which have a calming, soothing or relaxing activity; substances which have an activity in stimulating skin microcirculation in order to improve the radiance of the complexion, in particular of the face; substances which have a sebum-regulating activity, for the care of greasy skin; substances intended to cleanse or purify the skin; substances which have a free-radical scavenging activity; substances intended to reduce or delay the effects of skin aging, in particular the formation of wrinkles, through an activity aimed at promoting maintenance of the structure of the skin and/or at limiting degradation of the extracellular matrix of the superficial layers of the dermis and of the epidermis and/or at obtaining a protective, corrective or restructuring effect on the skin; substances which have an anti-inflammatory activity.

In addition to the dyestuff according to the invention, the compositions can advantageously comprise at least one excipient chosen from pigments, nacres, dyes, polymers, surfactants, rheology agents, fragrances, electrolytes, pH modifiers, antioxidants, preservatives, and mixtures thereof.

The dyestuffs of the invention are particularly useful as pigments in cosmetic compositions, and in particular in cosmetic compositions intended for making up the skin or superficial body growths.

The invention also relates particularly preferably to the use of the dyestuff of the invention prepared from the arils of seeds of the plant species *Ravenala madagascariensis*, as a coloring agent, in colored or coloring compositions capable of including same, and more particularly in cosmetic compositions, in particular compositions intended for making up the skin or superficial body growths such as the eyelashes.

It will be noted that, in the case of the cosmetic compositions, the presence of the wax can constitute an advantage and that, in this case, there will be no need to separate it from the rest of the colored product. In particular, in the case of *Ravenala madagascariensis* arils, the wax collected is very fine and can prove to be attractive for certain compositions, in particular cosmetic compositions.

Those skilled in the art will readily understand that the amount of dyestuff contained in the compositions of the invention depends to a great extent on the type of composition and on the desired effect.

In general, and more particularly in the cosmetics field, the dyestuff of the invention may be used to obtain either a colored composition or a coloring composition. Those skilled in the art will understand that the amounts of dyestuff in these two types of composition will necessarily be different and will, of course, depend on the nature of this dyestuff.

By way of example, more specifically in the cosmetics field, it will be possible to seek to color a composition, for example a cosmetic care composition, the aim of which is not to color the skin.

In particular, in the case of the use of the vivid blue-colored dyestuff extracted from the arils of the *Ravenala madagascariensis* plant, it will be possible for those skilled in the art to select the amount of this dyestuff which is just sufficient to obtain a blue-tinge effect in a white care composition, such as a cream.

It will also be possible to color a cosmetic composition of which the function is to color the skin or superficial body growths, for the purpose of obtaining a coloring composition, in particular a composition intended for makeup.

In the particular case where the dyestuff is obtained from the arils of the seeds of the species *Ravenala madagascariensis*, this dyestuff will preferably be used in compositions comprising a fatty phase and intended to color the skin or superficial body growths. This composition will, for example, be a mascara or a lipstick.

The invention also relates to a process for making up the skin or superficial body growths, in particular the eyelashes, the hair or the nails, comprising the application, to at least a part of the skin or superficial body growths, of a composition as described above.

Example 1: Preparation of a Dyestuff of the Invention, in the Form of a Colored Wax, from Arils of Seeds of *Ravenala madagascariensis*

A dyestuff according to the invention is prepared according to the following steps:

1—100 g of arils of seeds of *Ravenala madagascariensis* are placed in the tank of an ultrasonic extractor equipped with 4 piezoelectric devices (=400 W), with two liters of osmosed water to which 2 ml of aqueous ammonia at 20% (22° Be) have been added.

2—In order to carry out a decompartmentalization of the plant cells, sonication is performed (submission of the plant material to ultrasound). Said sonication is carried out at 55° C. (starting temperature) for approximately 10 minutes, at a frequency of 27 kHz. During this operation, no notable change in temperature occurs (the effect of the cavitation of the ultrasound creates an increase in temperature which compensates for the losses due to spontaneous cooling).

3—After this step, a first filtration is carried out on a sieve or a screen printing cloth in order to eliminate mainly the cellulosic residues. The aqueous filtrate is in the form of a blue milk, containing saponified wax.

4—The arils retained by the filter are recovered and the sonication is repeated under the same conditions as those specified above (time, temperature, proportions of aqueous ammonia, etc.).

5—After filtration of the aqueous phase of this further sonication operation, the filtered juices are combined.

6—The aqueous phase thus obtained is then acidified to approximately pH 4 by adding 9 ml of 75% acetic acid. The effect is immediate: the color, the wax flocculates, entraining with it the blue pigment, and deposits on cooling.

7—The process is accelerated in the refrigerator (temperature of approximately 4° C.). The supernatant water is removed, and the waxy blue precipitate is washed twice with osmosed water in order to remove the traces of ammonium acetate which has formed and also the residual acid.

8—The waxy blue precipitate which is still cold is then recovered by filtration on a paper filter, of Joseph paper type. The filtrate is clear.

9—The filter retaining the blue wax is dried at 25° C. in order to eliminate as much water as possible.

This method makes it possible to obtain approximately 30 g of colored wax per 100 g of starting arils.

This colored wax constitutes a dyestuff according to the invention. The color thereof is a vivid blue.

It may be used as a pigment or coloring agent for coloring the compositions of the invention.

Example 2: Method for Preparing a Dyestuff of the Invention, in the Form of a Colored Wax, from Arils of Seeds of *Ravenala madagascariensis*

According to a method different than that described above in example 1, the arils of seeds of *Ravenala madagascariensis* are covered with ethyl acetate or acetone and then the whole is placed in an ultrasonic extractor tank of the type of that of example 1. They are then subjected to the action of ultrasound in order to perform the cell decompartmentalization, at the frequency of approximately 27 kHz for a few minutes, until the plant material has been exhausted, and then the extract is filtered. The sonication lasts approximately 10 minutes. The wax released dissolves in the organic solvent.

The organic phase thus obtained is then supplemented with half of its volume of water. The addition of water causes a release of the wax, which, from that moment, flocculates in the aqueous phase, entraining with it the blue pigment. The aqueous phase containing the flocculated colored wax is then separated by settling out.

In order to enrich this aqueous phase with blue dyestuff, the following procedure is carried out.

An extraction with new arils is carried out as described previously. The organic phase obtained after sonication is filtered, and then added to the previously reserved aqueous phase. The colored waxy extract contained in the aqueous phase in the flocculated state is thus enriched and its color becomes more vivid. The operation can be repeated up to four times always with the same aqueous phase.

At the end of this enrichment step, the colored wax is separated from the aqueous phase by filtration on extra thin paper, such as a commercially available paper called "Joseph paper".

It will be observed that, in this case, a waxy residue is obtained which has a much more vivid color than that obtained with the method of the previous example. This residue is in fact more concentrated in blue pigment, since in particular a significant part of the wax remained in solution in the solvent, whereas virtually all the blue pigment was entrained in the wax having flocculated.

Finally, the colored waxy residue thus obtained is free of the solvent and water residues by evaporation.

This very vividly colored waxy residue obtained at the end of the method described constitutes a dyestuff according to the invention.

Example 3: Anti-Aging Cosmetic Composition Comprising a Pigment According to the Invention The dyestuff obtained according to example 1 is added to the oily phase of an oil-in-water emulsion for the prevention of skin aging, the formula of which is described below:

The percentages are expressed by weight relative to the final composition:

| | |
|---|---|
| *Centella asiatica* plant extract | 0.1 |
| Blue dye according to example 1 | 2 |
| Surfactant (Arlacel ® 165 VP) | 5 |
| 95% cetyl alcohol | 1 |
| Stearyl alcohol | 1 |
| Beeswax | 1.5 |
| Oil (Perleam ®) | 8.5 |

| | |
|---|---|
| Tri caprate/caprylate glycerides | 3 |
| Silicone oil (dimethicone 100 CS) | 1 |
| Polymer (Keltrol ®) | 0.35 |
| Sodium hydroxide | 0.04 |
| Tetrasodium EDTA powder | 0.1 |
| Preservatives | 0.5 |
| Water | qs 100 |

The composition is a bluish-colored anti-aging cream, the activity of which is aimed at preventing or slowing down the signs of skin aging.

Example 4: Cosmetic Makeup Composition Comprising a Dyestuff According to the Invention The dyestuff obtained according to example 1 is added to the fatty phase of a mascara formula described below:

| | |
|---|---|
| Blue dye according to example 1 | 10 |
| C18-36 Triglycerides | 9.9 |
| Glyceryl stearate | 12.0 |
| Other dyes | 9.5 |
| Beeswax | 4.6 |
| Carnauba wax | 2.2 |
| Triethanolamine | 1.9 |
| SHELLAC | 1.9 |
| Stearic acid | 1.9 |
| Palmitic acid | 1.9 |
| Hydrogenated glyceryl rosinate | 1.5 |
| PVP/VA copolymer | 0.95 |
| Lecithin | 0.95 |
| Preservatives | 0.6 |
| Xanthan gum | 0.4 |
| Phenoxyethanol | 0.2 |
| Hydrolyzed keratin | 0.15 |
| Tetrasodium EDTA | 0.05 |
| Fragrances | qs |
| Water | qs 100 |

The mascara thus obtained is a vivid blue color.

The invention claimed is:

1. A method for extracting a blue colored wax from a *Ravenala madagascariensis* plant, said blue colored wax comprising iridisomes producing a blue coloration of said blue colored wax and a wax fraction; the method comprising the steps of:
    (a) mixing arils of seeds of the *Ravenala madagascariensis* plant with an alkaline aqueous medium and forming a basic solution;
    (b) adding an organic acid to the basic solution in an amount sufficient for adjusting pH of the mixture to 4 or less and forming a mixture comprising a blue colored wax in the form of precipitated flakes and cellulose-based residues; and
    (c) filtering the mixture of step (b), separating the blue colored wax from the cellulose-based residues and recovering the blue colored wax comprising iridisomes and a wax fraction from the mixture.

2. The method of claim 1, wherein the alkaline aqueous medium comprises ammonia.

3. The method of claim 1, wherein the organic acid comprises acetic acid.

4. The method of claim 1, further comprising maintaining the temperature of the basic solution in step (a) at about 60° C.

5. The method of claim 1, further comprising applying at least one external energy source to the basic solution during step (a).

6. The method of claim 5, wherein the external energy source comprises mechanical stirring, homogenizing, milling, ultrasound, or a combination thereof.

7. A method for preparing a cosmetic composition comprising extracting a blue colored wax according to the method of claim 1, further comprising a step of mixing the blue colored wax with an oily phase.

* * * * *